(12) United States Patent
Blackwell et al.

(10) Patent No.: US 7,621,282 B2
(45) Date of Patent: Nov. 24, 2009

(54) PROBE WASHING CUPS AND METHODS

(75) Inventors: Gregory A. Blackwell, Dallas, TX (US); Ganesh Rajagopal, Carrollton, TX (US)

(73) Assignee: Abbott Laboratories, Inc., Abbott Park, IL (US)

( * ) Notice: Subject to any disclaimer, the term of this patent is extended or adjusted under 35 U.S.C. 154(b) by 887 days.

(21) Appl. No.: 10/869,992

(22) Filed: Jun. 17, 2004

(65) Prior Publication Data

US 2005/0279387 A1 Dec. 22, 2005

(51) Int. Cl.
*B08B 9/00* (2006.01)
*B08B 3/00* (2006.01)
*G01N 35/10* (2006.01)

(52) U.S. Cl. .................. 134/22.1; 134/88; 134/22.12; 134/61

(58) Field of Classification Search ............ 134/88, 134/22.1, 22.11, 22.12, 22.14, 22.18, 22.19; 422/100
See application file for complete search history.

(56) References Cited

U.S. PATENT DOCUMENTS

| | | | |
|---|---|---|---|
| 3,266,322 A | * | 8/1966 | Negersmith et. al. ..... 73/864.22 |
| 4,516,437 A | | 5/1985 | Pedroso et al. |
| 4,989,623 A | | 2/1991 | Hoffman et al. |
| 5,603,342 A | * | 2/1997 | Shambaugh ................ 134/154 |
| 6,422,248 B1 | | 7/2002 | Fürst et al. |
| 2002/0066717 A1 | * | 6/2002 | Verhaverbeke et al. ........ 216/13 |

FOREIGN PATENT DOCUMENTS

| | | |
|---|---|---|
| EP | 0 725 279 | 8/1996 |
| JP | 62-242858 | 10/1987 |
| JP | 62242858 | * 10/1987 |
| WO | 97/03766 | 2/1997 |
| WO | WO9942810 | * 8/1999 |
| WO | WO 9942810 | * 8/1999 |

* cited by examiner

*Primary Examiner*—Michael Kornakov
*Assistant Examiner*—Stephen Ko
(74) *Attorney, Agent, or Firm*—David L. Weinstein

(57) ABSTRACT

The invention provides probe washing cups and methods. A probe washing cup has a washing well and a waste cup. A drying section is disposed between an open end of the probe washing cup and an inlet plane of the washing well. The drying section has a channel that is aligned with the washing well. The channel has an opening for receiving the probe therethrough.

11 Claims, 12 Drawing Sheets

PROBE WASHING CUPS AND METHODS

TECHNICAL FIELD OF THE INVENTION

The present invention relates generally to probe cleaning and in particular the present invention relates to probe washing cups and methods.

BACKGROUND OF THE INVENTION

Automated medical analyzers perform medical tests on a sample, such as biological liquids, e.g., whole blood, blood plasma, blood serums, urine, etc. These tests may require mixing of the sample with a liquid, such as a reagent. Once the sample is mixed with the liquid, a chemical reaction may take place. The chemical reaction can be used to provide a medical professional with medical information about the sample and thus a medical condition of a patient.

Liquids, such as samples and reagents, are often moved from one location within the analyzer, such as sample or reagent vials moved on carousels, to another location within the analyzer, such as test region, e.g., having test tubes or the like. Many analyzers use a hollow probe carried by a robot arm to accomplish this. Specifically, the probe is inserted into the liquid, and some of the liquid is drawn into the probe. The liquid is subsequently expelled from the probe into the test tube for testing.

One problem is that the probe becomes contaminated on its interior and exterior with the liquid and cannot be used for another liquid while contaminated. One method for dealing with contamination is to connect a disposable probe tip to the probe. In operation, the tip is inserted into the liquid, and the liquid is drawn into the tip. The liquid is then expelled, and the tip is replaced with a new tip for the next liquid. However, this becomes impractical and expensive for many analyzers.

Some analyzers reuse the same probe for successive tests and clean the probe between each test. One method for cleaning the probe involves pumping a cleaning liquid, such as a buffer, through the probe while the probe tip is inserted into a shallow cup. The cleaning liquid exits the probe tip and fills the cup to immerse the tip in the cleaning liquid. Then, the cleaning liquid is pumped onto the exterior of the probe. One problem with this is that separate pumps are usually used to pump the cleaning liquid through the probe and onto the probe exterior. Another problem is that the cleaning liquid is directed at a single location on the probe exterior, making it difficult to clean the entire probe exterior. Other problems include increased wash times, an increased volume of cleaning liquid, and/or increased operating pressures.

For the reasons stated above, and for other reasons stated below which will become apparent to those skilled in the art upon reading and understanding the present specification, there is a need in the art for alternative probe cleaning apparatus and methods.

SUMMARY

The above-mentioned problems with probe cleaning apparatus and methods and other problems are addressed by the present invention and will be understood by reading and studying the following specification.

For one embodiment, the invention provides a probe washing cup having a washing well and a waste cup. A drying section is disposed between an open end of the probe washing cup and an inlet plane of the washing well. The drying section has a channel that is aligned with the washing well. The channel has an opening for receiving the probe therethrough.

For another embodiment, the invention provides a medical analyzer having a hollow probe for transporting substances within the medical analyzer, a wash cup for washing the probe, and a controller for controlling operation of the medical analyzer. The wash cup has a washing well and a waste cup. A drying section is disposed between an open end of the wash cup and an inlet plane of the washing well. The drying section has a channel that is aligned with the washing well. The channel has an opening for receiving the probe therethrough.

For another embodiment, the invention provides a method of cleaning a hollow probe. The method includes inserting a length of the probe into a washing well of a wash cup containing a cleaner for cleaning an exterior of the active length. Drawing a cleaner from the washing well into the probe and expelling the cleaner from the probe by forcing additional cleaner through the probe into the washing well are included in the method. The method includes extracting the probe from the washing well. Directing a forced airflow over an exterior of the probe while extracting the probe from the washing well, where the forced airflow acts to dry the exterior of the probe, is included in the method.

Further embodiments of the invention include methods and apparatus of varying scope.

DETAILED DESCRIPTION

Figure 1:
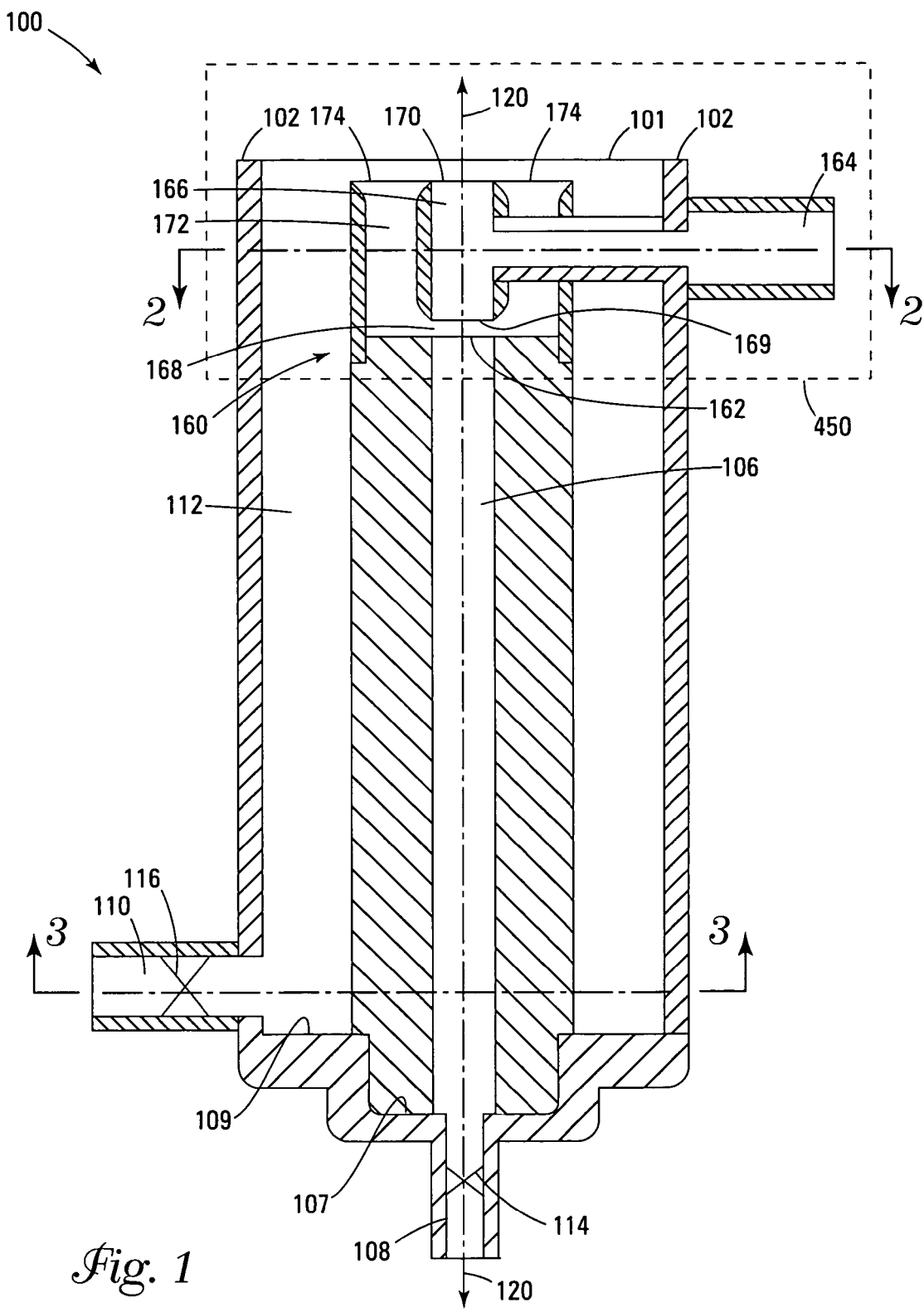
FIG. 1 is a cross-sectional elevation view of a wash cup, according to an embodiment of the present invention.

In the following detailed description of the invention, reference is made to the accompanying drawings that form a part hereof, and in which is shown, by way of illustration, specific embodiments in which the invention may be practiced. In the drawings, like numerals describe substantially similar components throughout the several views. These embodiments are described in sufficient detail to enable those skilled in the art to practice the invention. Other embodiments may be utilized and structural, logical, and electrical changes may be made without departing from the scope of the present invention. The following detailed description is, therefore, not to be taken in a limiting sense, and the scope of the present invention is defined only by the appended claims and equivalents thereof.

Figure 2:
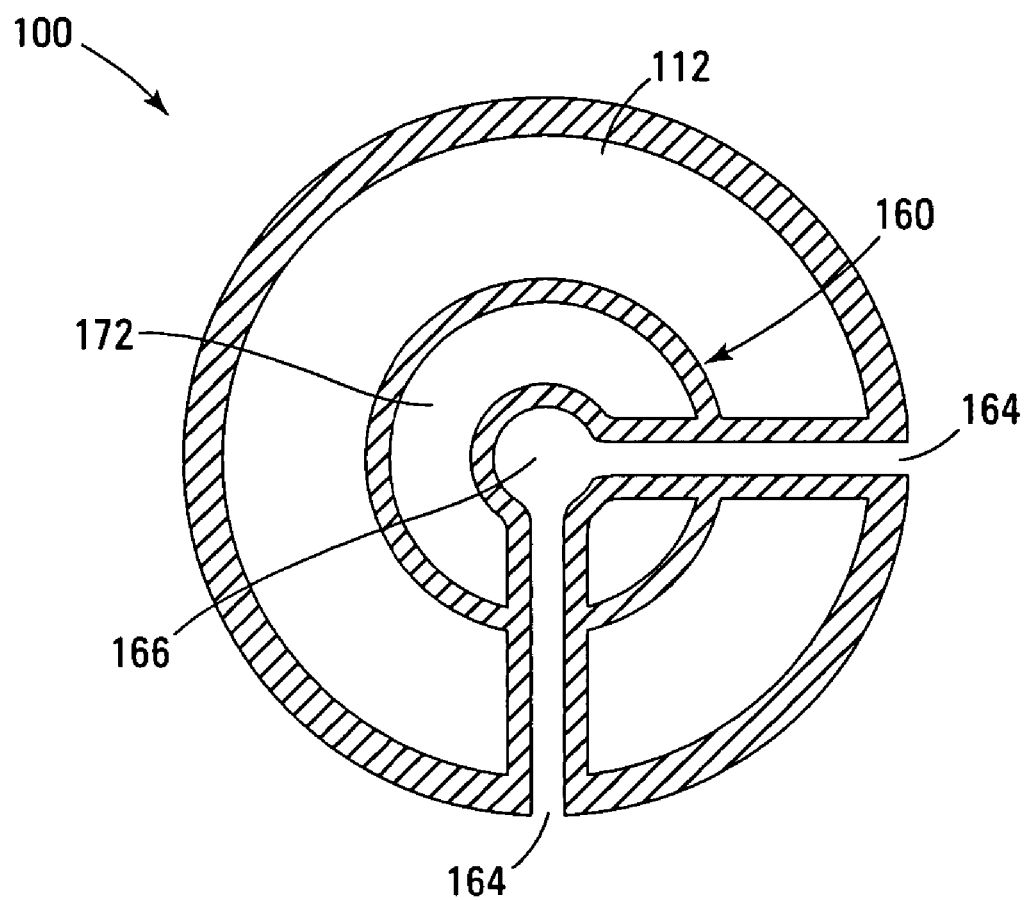
FIG. 2 is a cross-section viewed along line 2-2 of FIG. 1.
Figure 3:
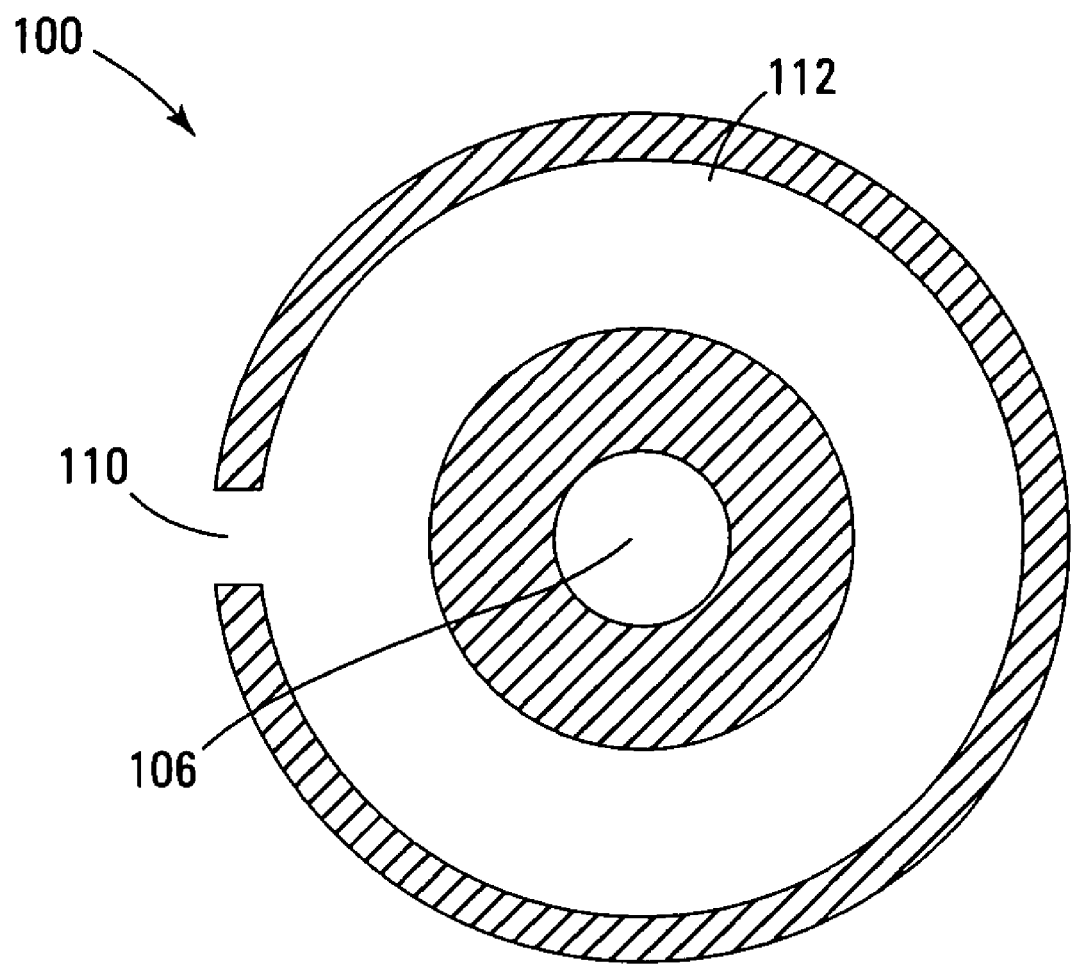
FIG. 3 is a cross-section viewed along line 3-3 of FIG. 1.
Figure 4:
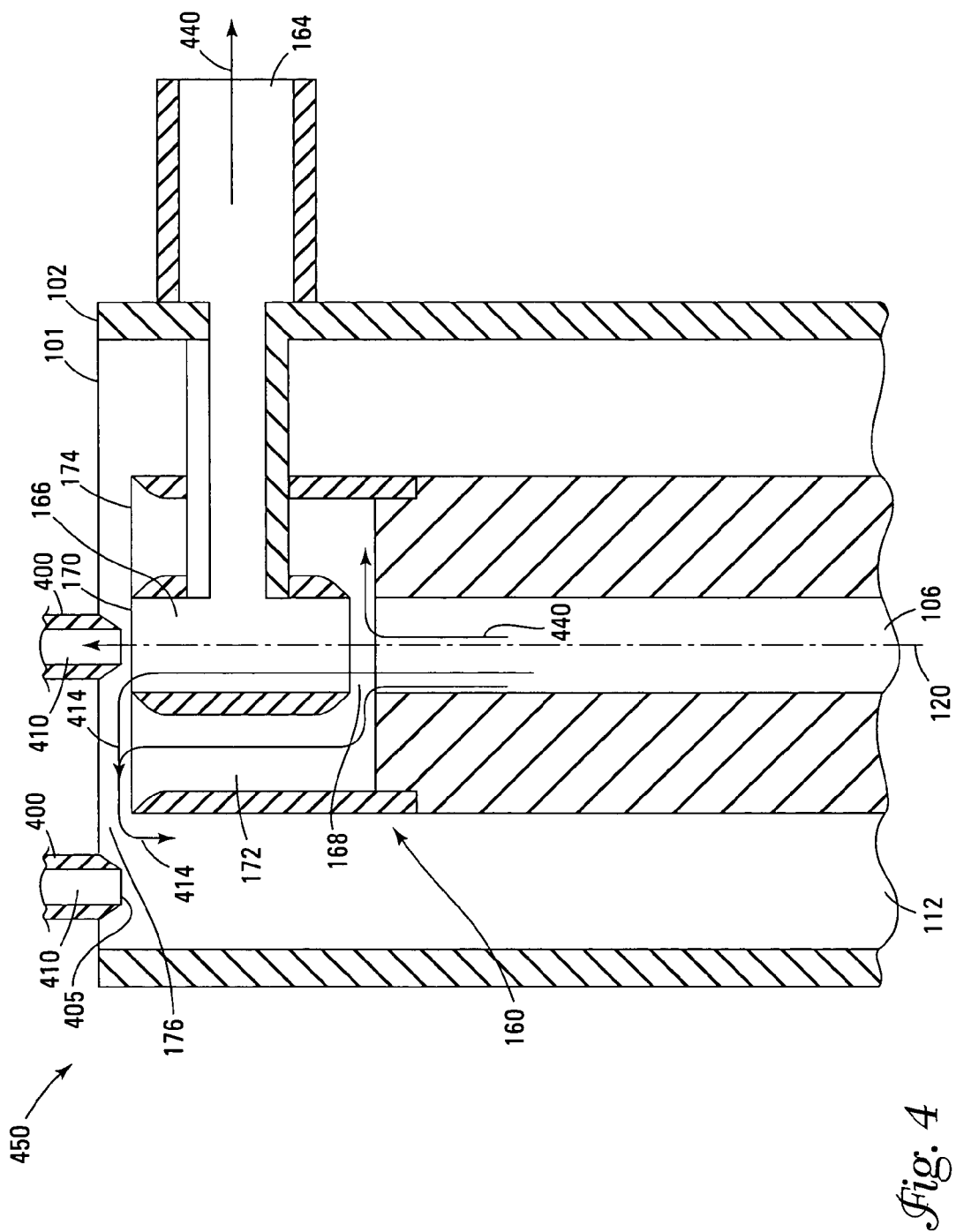
FIG. 4 is an enlarged view of region 450 of FIG. 1 showing the wash cup of FIG. 1 during operation, according to another embodiment of the present invention.

FIGS. 1-4 illustrate a wash cup 100, e.g., of a medical analyzer, for probes, according to an embodiment of the present invention. Specifically, FIG. 1 is a cross-sectional elevation view, FIG. 2 is a cross-section viewed along line 2-2 of FIG. 1, FIG. 3 is a cross-section viewed along line 3-3 of FIG. 1, and FIG. 4 is an enlarged view of region 450 of FIG. 1.

Wash cup 100 has an opening 101 at an upper end 102, as shown in FIGS. 1 and 4. Wash cup 100 includes a first longitudinal compartment (or washing well) 106. A drain 108 is disposed, for one embodiment, between a lower end 107 of washing well 106 and the exterior of wash cup 100, as shown in FIG. 1, for draining washing well 106, e.g. under gravitational force, vacuum pressure, etc. Wash cup 100 also includes a second longitudinal compartment (or waste cup) 112 that is substantially parallel to washing well 106. A drain 110 is disposed between waste cup 112 and the exterior of wash cup 100 adjacent a lower end 109 of waste cup 112, as shown in FIG. 1, for draining waste cup 112, e.g. under gravitational force, vacuum pressure, etc.

For one embodiment, valves 114 and 116 selectively open and close drains 108 and 110, respectively. Valves 114 and 116 may be respectively disposed in drains 108 and 110, as shown in FIG. 1, or may be part of external plumbing connectable to drains 108 and 110. For another embodiment, valves 114 and/or 116 are electrically actuatable valves, such as solenoid valves, pneumatically actuatable valves, or the like. For another embodiment, valves 114 and 116 are electrically connectable to a controller of an automated medical analyzer for actuation thereby. For another embodiment, drains 108 and 110 are connectable to a vacuum system, e.g., of the automated medical analyzer. For another embodiment, the controller of the automated medical analyzer controls the vacuum system.

A drying section 160 is disposed between an inlet 162 of washing well 106 and end 102, as shown in FIGS. 1 and 4. Drying section 160 includes a longitudinal central channel 166 that serves as an inlet channel to washing well 106 and that is substantially parallel to waste cup 112. A gap 168 separates an exit plane 169 of channel 166 from inlet plane 162 of washing well 106, as shown in FIG. 1. Central channel 166 has an opening (or inlet plane) 170 that is open to the exterior of wash cup 100, as shown in FIGS. 1 and 4 for receiving a probe. One or more flow (or aspiration) channels 164 extend radially outward, for one embodiment, from central channel 166 to an exterior of wash cup 100, as shown in FIGS. 1, 2 and 4. For another embodiment, aspiration channels 164 are connectable to the vacuum system or to air pressures greater than atmospheric pressure.

Drying section 160 has a longitudinal internal passage (or channel) 172 that is disposed between central channel 166 and waste cup waste cup 112 and that is substantially parallel to central channel 166, as shown in FIG. 4. Internal flow passage 172 has an opening (or inlet plane) 174 that for one embodiment is substantially coplaner with inlet plane 170, as shown in FIGS. 1 and 4. For another embodiment, inlet plane 170 is recessed from end 102 of wash cup 100, as is inlet plane 174. That is, a recess 176 separates inlet planes 170 and 174 of drying section 160 from end 102, as shown in FIG. 4. Gap 168 communicatively couples washing well 106 and central channel 166 to internal passage 172, as shown in FIG. 4.

For one embodiment, washing well 106 has a circular cross-section, as shown in FIG. 3, the center of which coincides with a central longitudinal axis 120 of wash cup 100, as shown in FIG. 1. Waste cup 112 is coaxial with wash cup 106 and, for one embodiment, has an annular cross-section, as shown in FIG. 3. Drying section 160 is coaxial with waste cup 112, as shown in FIG. 2. More specifically, channel 166 has a circular cross-section and is coaxial with waste cup 112. Internal passage 172 is coaxial with channel 166 and waste cup 112 and has an annular cross-section, as shown in FIG. 2.

Note that for one embodiment, channel 166 and washing well 106 are substantially axially aligned along axis 120. Also note that inlet plane 170 of channel 166 and inlet plane 174 of internal passage 172 are coaxial inlet planes (or openings) to drying section 160.

In the event that the washing well 106 is filled with a liquid, such as a cleaning liquid, so that the liquid overflows into drying section 160, gap 168, internal channel 172, and central channel 166 direct the liquid into waste cup 112 through recess 176, as shown by arrows 414 in FIG. 4. The liquid can be drained from waste cup 112 through drain 110 upon opening valve 116.

In operation, an end (or tip) 405 of a hollow probe 400 is positioned in recess 176, i.e., at level between inlet plane 170 of channel 166 and end 102 of wash cup 100 above waste cup 112 so that probe 400 aligns with waste cup 112, as shown in FIG. 4, e.g., using a robot arm of an automated medical analyzer or the like. For one embodiment, a cleaning liquid, such as a buffer, is then added to probe 400, e.g., by pumping the cleaning liquid from a cleaning-liquid reservoir of the medical analyzer using a syringe, a pump, or a combination thereof. In other embodiments the cleaning-liquid reservoir may be external to the medical analyzer. The cleaning liquid flows into an interior 410 of probe 400 toward the end 405 of probe 400 and waste cup 112 for filling interior 410 with the cleaning liquid without allowing the cleaning liquid to flow through probe 400 into waste cup 112. For another embodiment, the cleaning liquid is allowed to flow through probe 400 into waste cup 112 for expelling a contaminant, such as residual reagent or residual from a sample, e.g., blood serum, blood plasma, or other biological liquid, from interior 410 of probe 400 into waste cup 112. The flow is then stopped, with the cleaning liquid filling interior 410. For one embodiment, the volume of cleaning liquid that flows through probe 400 into waste cup 112 is about the volume of interior 410 of probe 400.

Probe 400 is then positioned above central channel 166 of drying section 160, e.g., by the robot arm, and is substantially aligned with axis 120 of wash cup 100, so that the end of the probe is positioned between inlet plane 170 of central channel 166 and end 102 of wash cup 100, i.e., in recess 176, as shown in FIG. 4. For one embodiment, the distance between probe end 405 and end 102 of wash cup 100 remains fixed while probe 400 is moved from wash cup 112 location to above drying section 160. While probe 400 is in this position, a volume of air, e.g., about 1 to about 3 percent of the volume of probe interior 410, may be drawn into probe 400 using a syringe, a pump, or a combination thereof, to form an air gap between the cleaning liquid and end 405. The air, in turn, will form an air gap between the cleaning liquid and any cleaning liquid subsequently drawn into probe 400, such as from washing well 106, as described below. For one embodiment, the volume of air is drawn into probe 400 as the probe moves from waste cup 112 into substantial alignment with axis 120.

Figure 5:
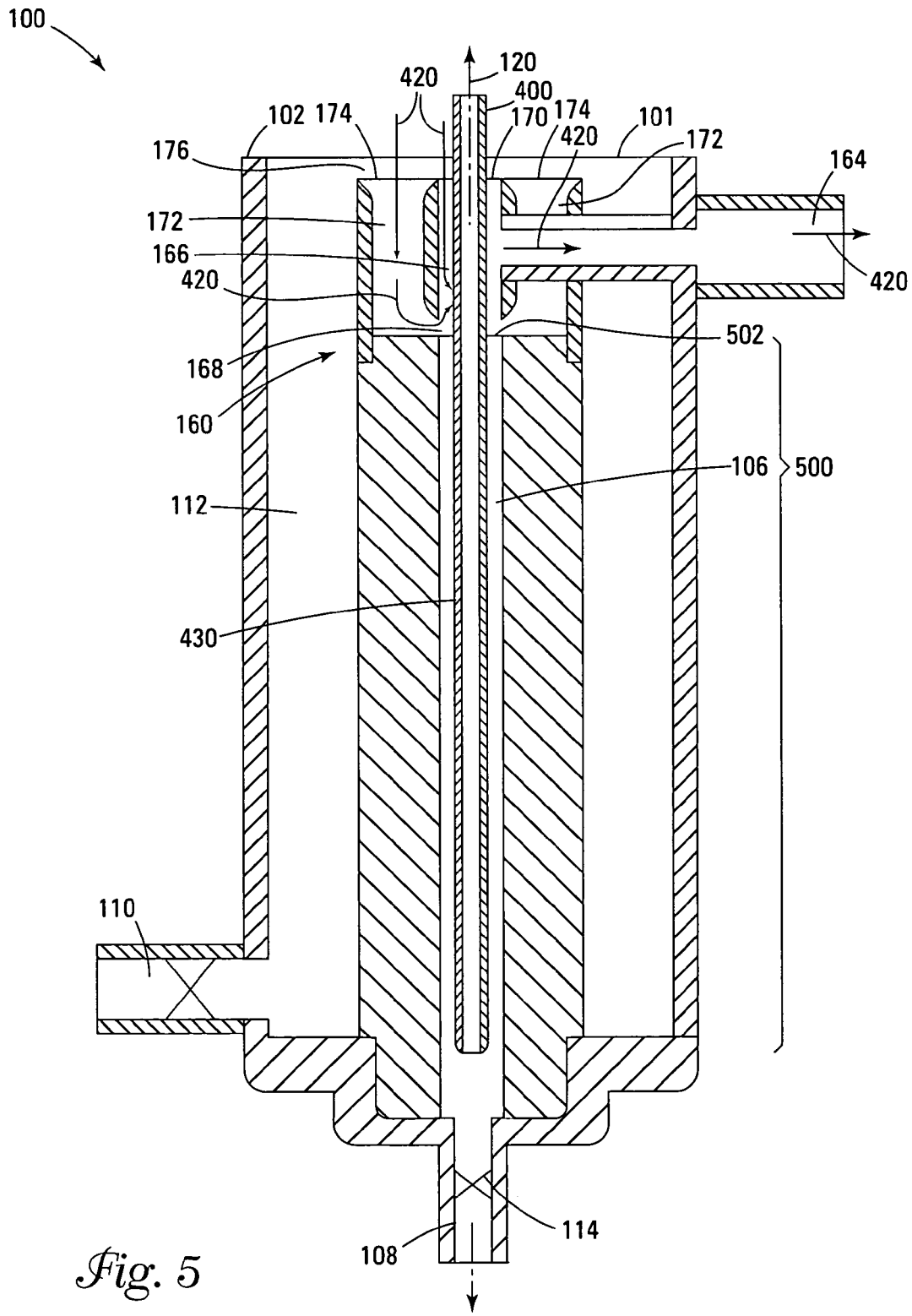
FIG. 5 is cross-sectional elevation view of a wash cup during operation, according to another embodiment of the present invention.

A length 500 of probe 400 is then inserted into the cleaning liquid contained in washing well 106, as shown in FIG. 5, at a relatively high insertion rate. For one embodiment, the length 500 is at least a length to which the contaminant has wetted the probe internally and/or externally, but can be any fraction of the entire length of probe 400, including the entire length. For one embodiment, washing well 106 is filled with cleaning liquid, e.g., drawn from the cleaning-liquid reservoir, to a level 502 that is sufficient to wet the probe exterior along the length 500, as shown in FIG. 5. For some embodiments, an external pump fills the washing well 106.

Cleaning liquid is then drawn into probe 400 from washing well 106 to a level that is at least the level that a reagent or sample is drawn into probe 400 during use, e.g., the level 502. Drawing the cleaning liquid into probe 400 from washing well 106 simulates drawing a reagent or sample into probe 400 during use. For one embodiment, the cleaning liquid is drawn into probe at about the same rate as a sample or reagent is drawn in during use. For one embodiment liquid is drawn into the probe from the washing well using a syringe, a pump, or a combination thereof.

An internal probe wash that includes forcing additional cleaning liquid through probe 400, e.g., that is drawn from the cleaning-liquid reservoir using a pump, syringe, etc., into washing well 106 is subsequently performed. This expels any cleaning liquid previously contained in the probe into washing well 106. For one embodiment, as the cleaning liquid is forced through probe 400, probe 400 is extracted from washing well 106 at a relatively low extraction rate, and a vacuum is applied to aspiration channels 164. For another embodiment, probe 400 is extracted after the cleaning liquid is forced through probe 400. For another embodiment, the extraction rate is less than the insertion rate, e.g., about ¼ the insertion rate.

Applying the vacuum draws air from the exterior of wash cup 100 through inlet plane 170 of central channel 166 and inlet plane 174 of internal passage 172, as shown by arrows 420 in FIG. 5. The air flows over the exterior surface 430 of probe 400 and acts to dry exterior surface 430 as probe 400 is extracted. Specifically, arrows 420 show that the air is directed in a first direction through channel 166 and that the air is directed through internal channel 172, through gap 168, and through channel 166 in a second direction substantially opposite the first direction. Note that for one embodiment, internal probe washing, drying the probe exterior, and extracting the probe from washing well 106 occur substantially simultaneously. The relatively low extraction rate increases the residence time of the probe within drying section 160, which results in more complete drying of the probe exterior. For other embodiments, air can be forced (or blown) into drying section 160 from an exterior of wash cup 100 through aspiration channels 164 and onto probe 400 as it is extracted to dry its exterior surface 430.

For some embodiments, valve 114 of drain 108 is opened at the start of the internal probe wash for a preselected time sufficient to substantially empty washing well 106. The cleaning liquid can be drained from washing well 106 under gravitational force or by applying a vacuum to drain 108. For other embodiments, washing well 106 drains substantially faster than the cleaning liquid is added to washing well 106. After valve 114 is closed, the cleaning liquid flows through probe 400, as probe 400 is extracted, and fills washing well 106 to the level 502, e.g., substantially to inlet plane 162 of washing well 106. For one embodiment, washing well 106 is filled and drained multiple times during the internal probe wash.

For one embodiment, the volume of cleaning liquid that passes through probe 400 during the internal probe wash exceeds the volume of washing well 106, e.g., by about a factor of 1.1 to about a factor of 4, and the excess cleaning liquid is drawn through drying section 160 and out aspiration channel 164 while extracting probe 400 from washing well 106. For some embodiments, if end 405 of probe 400 is extracted to about inlet plane 162 of washing well 106 before the end of the internal probe wash, i.e., before the cleaning liquid stops flowing through probe 400, extraction of probe 400 is stopped with end 405 substantially at inlet plane 162 until the cleaning liquid stops flowing. Any excess cleaning liquid that flows through probe 400 into the washing well is drawn through drying section 160 and out aspiration channel 164 while probe 400 is stopped at this position. Extraction of probe 400 then continues until end 405 is relocated between inlet plane 170 of central channel 166 and end 102, as shown in FIG. 4.

For some embodiments, the cleaning liquid is not drained from washing well 112. Instead, the excess cleaning liquid is drawn through drying section 160 and out aspiration channel 164, as described above.

Figure 6:
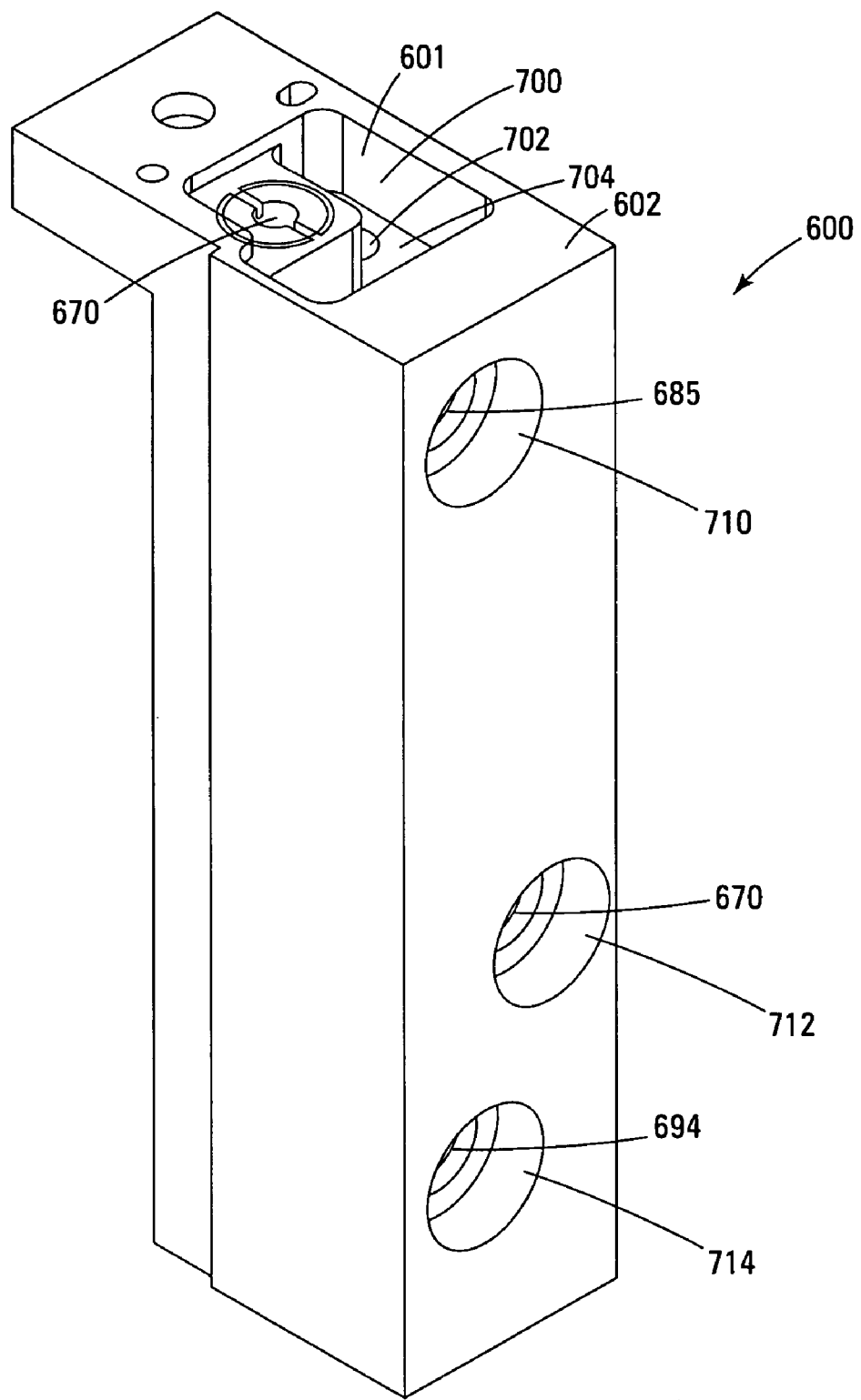
FIG. 6 is an isometric view of a wash cup, according to an embodiment of the present invention.
Figure 7:
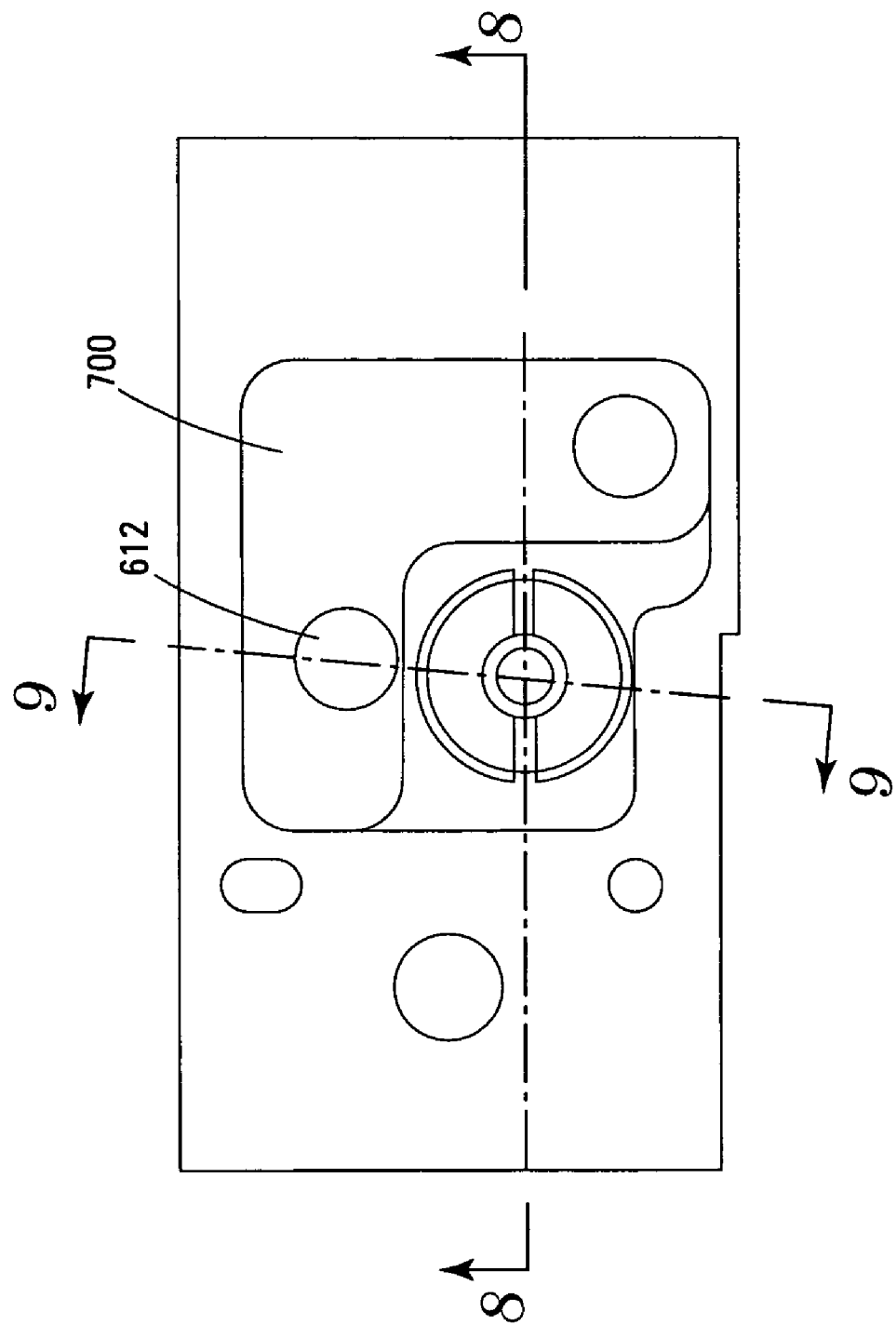
FIG. 7 is a top view of the wash cup of FIG. 6.
Figure 8:
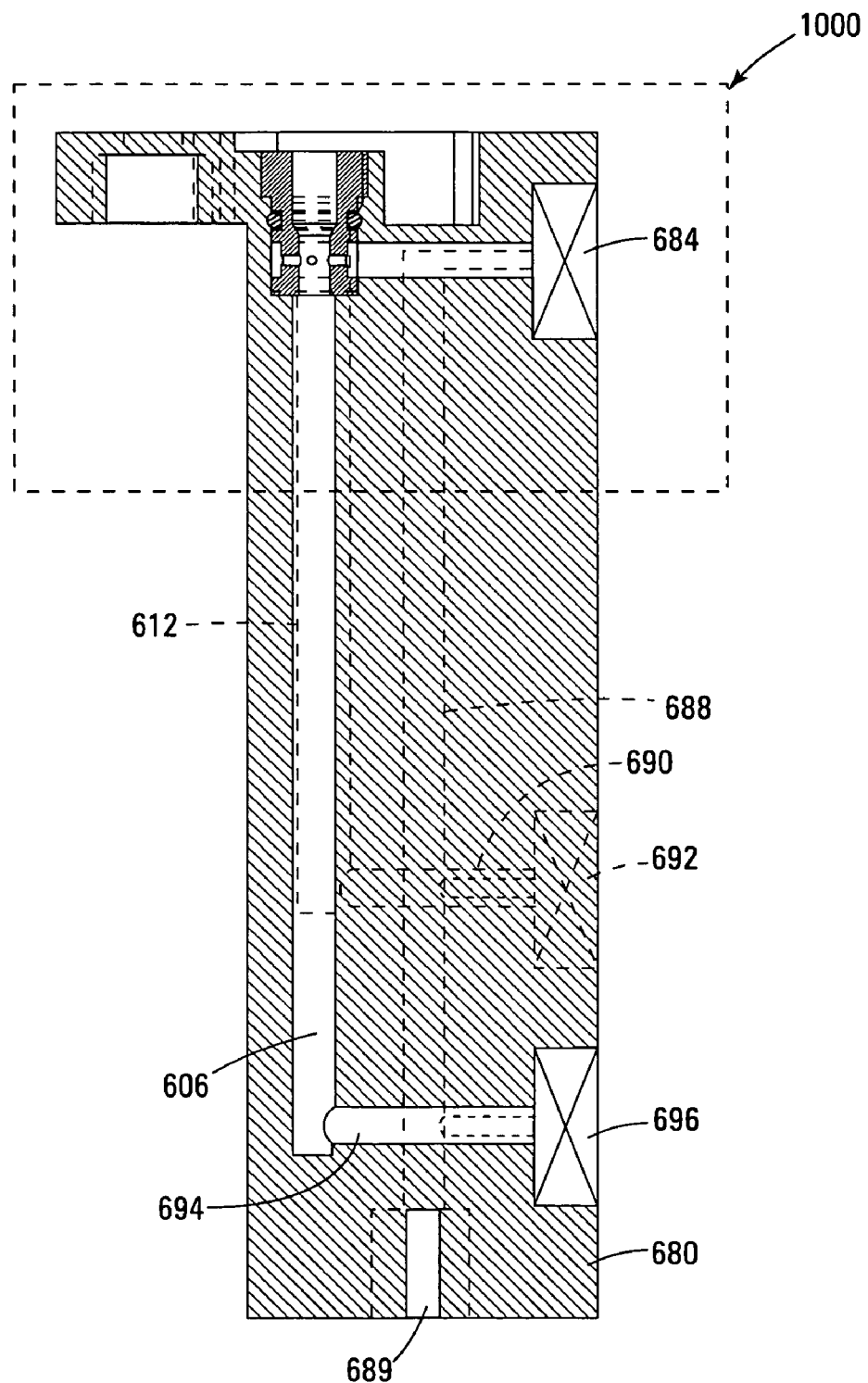
FIG. 8 is a view taken along line 8-8 of FIG. 7.
Figure 9:
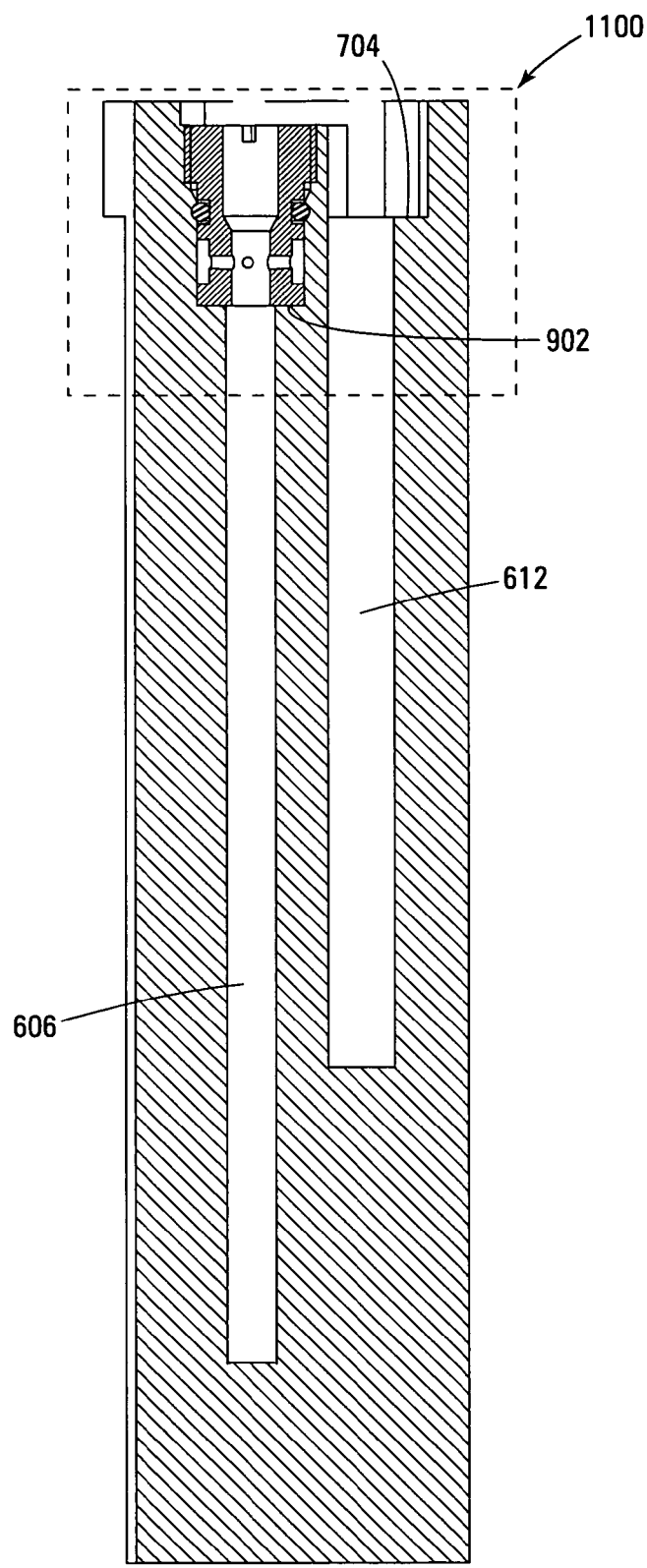
FIG. 9 is a view taken along line 9-9 of FIG. 7.
Figure 10:
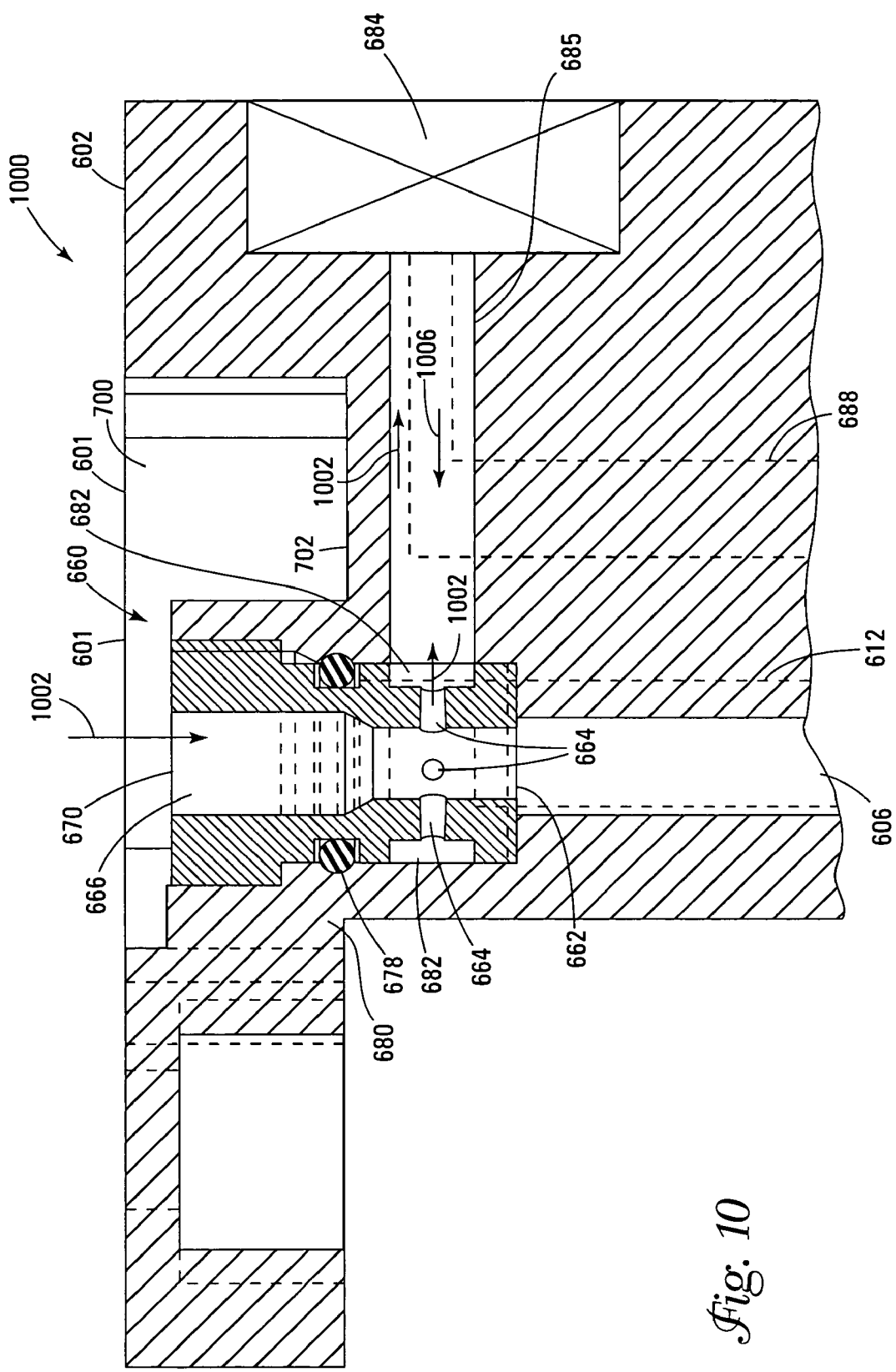
FIG. 10 is an enlarged view of region 1000 of FIG. 8.
Figure 11:
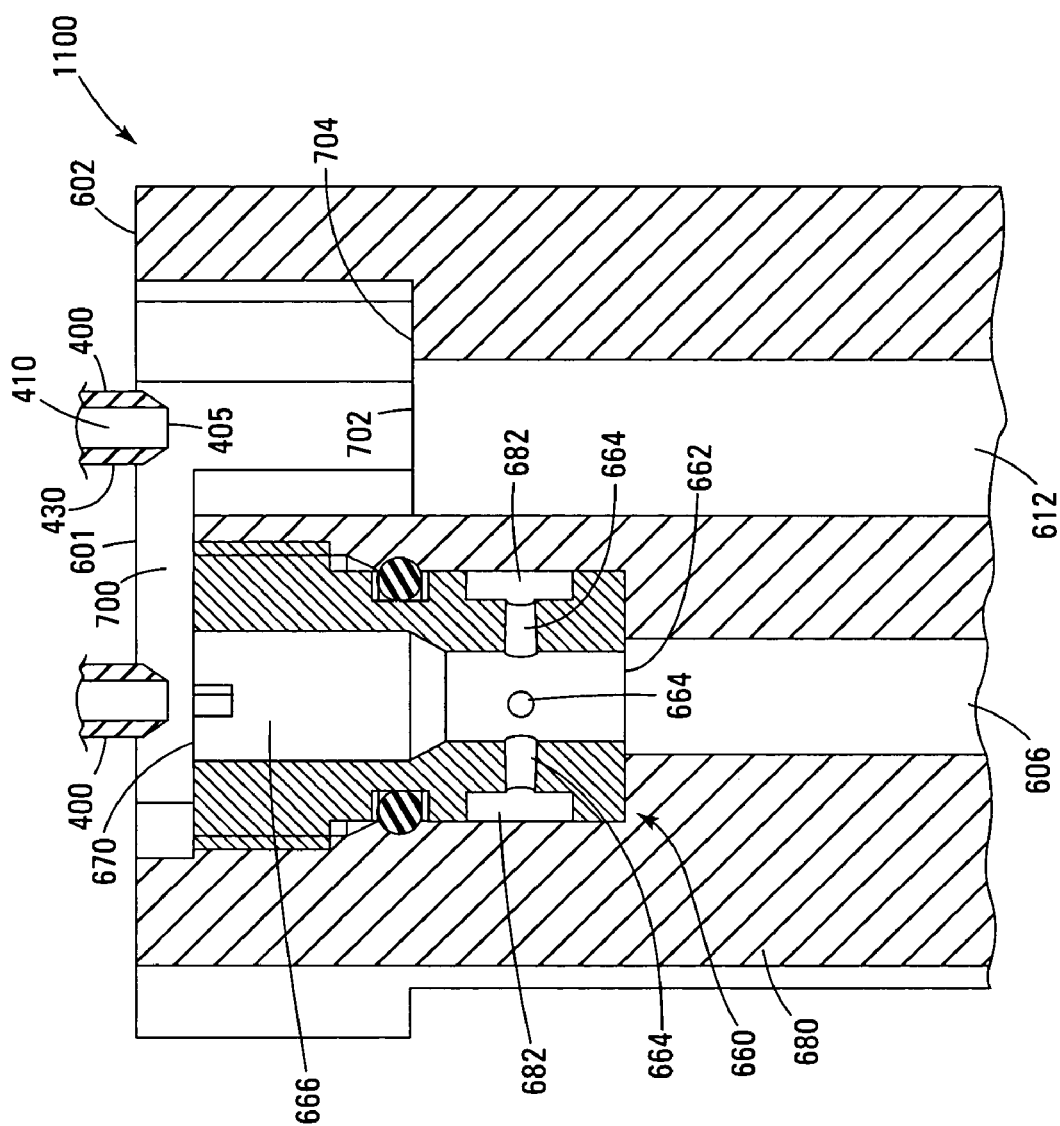
FIG. 11 is an enlarged view of region 1100 of FIG. 9.

FIGS. 6-11 illustrate a wash cup 600, e.g., of a medical analyzer, for probes, according to another embodiment of the present invention. FIG. 6 is an isometric view, FIG. 7 is a top view, FIG. 8 is a view taken along line 8-8 of FIG. 7, FIG. 9 is a view taken along line 9-9 of FIG. 7, FIG. 10 is an enlarged view of region 1000 of FIG. 8, and FIG. 11 is an enlarged view of region 1100 of FIG. 9.

Wash cup 600 has an opening 601 at an upper end 602, as shown in FIGS. 6, 10, and 11. Wash cup 600 includes a first longitudinal compartment (or washing well) 606 and a second longitudinal compartment (or waste cup) 612 located side by side and that are substantially parallel to each other, as best shown in FIGS. 9 and 11. A drying section 660 is disposed between an inlet (or inlet plane) 662 of washing well 606 and end 602, as shown in FIGS. 10 and 11. Drying section 660 includes a longitudinal central channel 666 that serves as an inlet channel to washing well 606 and that is substantially parallel to waste cup 612, as shown in FIGS. 10 and 11. Central channel 666 aligns with washing well 606 and has an opening (or inlet plane) 670 that is open to the exterior of wash cup 600, as shown in FIGS. 10 and 11, for receiving a probe, such as probe 400 of FIG. 4. For one embodiment, drying section 660 is an insert that is threaded into wash cup 600. For this embodiment, a seal 678, such as an O-ring, seals between the wash cup body 680 and the drying section. For another embodiment, washing well 606, waste cup 612, and central channel 666 have circular cross-sections.

One or more flow (or aspiration) channels 664 extend radially outward, for one embodiment, from central channel 666 to an annular flow channel 682 formed between drying section 660 and the wash cup body 680, as shown in FIGS. 10 and 11. Forming a slot in a sidewall of drying section 660 may form annular flow channel 682. The wash cup body 680 bounds the slot when drying section 660 is inserted into the wash cup body 680. For another embodiment, annular channel 682 is connected to a valve 684, such as an electrically actuatable valve, e.g., a solenoid valve, pneumatically actuatable valve, or the like, by a radial channel 685, as shown in FIG. 10. For some embodiments, valve 684 selectively fluidly couples radial channel 685, and thus central channel 666 via aspiration channels 664 and annular channel 682, to a manifold 688, as shown in FIGS. 8 and 10. For one embodiment, manifold 688 passes through the wash cup body 680 so that an end 689 of manifold 688 opens to an exterior of wash cup 100 and, for one embodiment, is connectable to a vacuum system, e.g., of an automatic analyzer. Therefore, valve 684 selectively fluidly couples drying section 660 to the vacuum system.

As best shown in FIG. 8, for one embodiment, a radial channel 690 connects waste cup 612 to a valve 692, such as an electrically actuatable valve, e.g., a solenoid valve, pneumatically actuatable valve, or the like. For some embodiments, valve 692 selectively fluidly couples radial channel 690, and thus waste cup 612, to manifold 688. Thus, valve 692 selectively fluidly couples waste cup 612 to the vacuum system. A radial channel 694 connects washing well 606 to a valve 696, such as an electrically actuatable valve, e.g., a solenoid valve, pneumatically actuatable valve, or the like. For some embodiments, valve 696 selectively fluidly couples radial channel 694, and thus washing well 606, to manifold 688. Thus, valve 696 selectively fluidly couples washing well 606 to the vacuum system. For another embodiment, valves 684, 692, and 696 are electrically connectable to a controller of an automated medical analyzer for actuation thereby.

FIGS. 6, 7, 10, and 11 show that, for one embodiment, wash cup 600 includes an overflow section 700 that is formed from a recess in upper end 602. Note that waste cup 612 and the drying section 660 open into overflow section 700. Specifically, for another embodiment, an inlet plane (or opening) 702 of waste cup 612 is substantially co-planer with a bottom 704 of overflow section 700, as shown in FIGS. 6 and 11. FIGS. 6 and 11 also show that, for another embodiment, drying section 660 protrudes from the bottom 704 of overflow section 700 so that the inlet plane 670 of drying section 660 is located between the bottom 704 of overflow section 700 and upper end 602. In the event that the washing well 606 is filled with a cleaning liquid so that the liquid overflows washing well 606 and drying section 660, the liquid can flow into overflow section 700 and into waste cup 612.

FIG. 6 illustrates that radial channels 685, 690, and 694 respectively open into holes 710, 712, and 714 that are countersunk into wash cup 600. Countersunk holes 710, 712, and 714 respectively receive valves 684, 692, and 696. For one embodiment, valves 684, 692, and 696 are respectively threaded into countersunk holes 710, 712, and 714.

As shown by arrows 1002 of FIG. 10, when valve 684 is open and a vacuum is applied to manifold 688, air is drawn through opening 601 of wash cup 600, through opening 670 of central channel 666 of drying section 660, through central channel 666, through aspiration channels 664, through annular flow channel 682, through radial channel 685, and into valve 684. The air flows through valve 684, e.g., into the plane of FIG. 10, and into manifold 688, as indicated by arrow 1006. The air acts to dry an exterior surface of a probe, such as the exterior surface 430 of probe 400 of FIG. 5, as the probe is extracted, as described above. Alternatively, drying can be accomplished by reversing the flow direction by applying an air pressure that is above atmospheric pressure to manifold 688 and blowing the air into drying section 660.

When valve 692 is open and a vacuum is applied to manifold 688, air is drawn into through opening 601 of wash cup 100, through opening 702 of waste cup 612, through waste cup 612, through radial channel 690, through valve 692, and into manifold 688 for removing any contaminants and cleaning liquid expelled from the probe into waste cup 632 or for removing any cleaning liquid that may have overflowed into overflow section 700 and waste cup 612, as described above. When valve 696 is open and a vacuum is applied to manifold 688, air is drawn into through opening 601 of wash cup 100, through opening 670 of central channel 666 of drying section 660, through washing well 606, through radial channel 694, through valve 696, and into manifold 688 for removing any contaminants and/or cleaning liquid from washing well 606. Alternatively, washing well 606 and/or waste cup 612 can be drained under gravitational force.

For one embodiment, wash cup 600 is operated to wash a probe, such as probe 400, in the same fashion as described above for wash cup 100. For another embodiment, probe is positioned within overflow section 700 so that probe 400 is aligned with waste cup 612 and so that end (or tip) 405 of probe 400 is positioned at level between inlet plane 670 of channel 666 and end 602 of wash cup 600, as shown in FIG. 11. With probe 400 so positioned, the method of operation described above when probe 400 is positioned above waste cup 112, as shown in FIG. 6 is repeated. That is, the probe 400 can be filled with cleaning liquid, e.g., from the cleaning-liquid reservoir, without allowing the cleaning liquid to flow through probe 400 into waste cup 612, or the cleaning liquid is allowed to flow through probe 400 into waste cup 612 for expelling a contaminant from interior 410 of probe 400 into waste cup 612. The flow is stopped, with the cleaning liquid filling interior 410.

Probe 400 is then positioned above central channel 666 so that the end 405 of probe 400 is positioned between inlet plane 670 of central channel 666 and end 602 of wash cup 600, as shown in FIG. 11. For one embodiment, the distance between probe end 405 and end 602 of wash cup 600 remains fixed while probe 400 is moved from the wash cup 612 location to above drying section 660. While probe 400 is in this position, a volume of air, e.g., about 1 to about 3 percent of the volume of probe interior 410, may be drawn into probe 400 to form an air gap between the cleaning liquid and end 405. The air, in turn, will form an air gap between the cleaning liquid and any cleaning liquid subsequently drawn into probe 400, such as from washing well 606, as described below. For one embodiment, the volume of air is drawn into probe 400 as the probe moves from waste cup 612.

The length 500 of probe 400, shown in FIG. 5, is then inserted into the cleaning liquid contained in washing well 606 at a relatively high insertion rate. For one embodiment, washing well 606 is filled with cleaning liquid, e.g., from the cleaning-liquid reservoir, to a level 902, shown in FIG. 9, that is sufficient to wet the probe exterior along the length 500. For one embodiment, an external pump accomplishes this.

Cleaning liquid is then drawn into probe 400 from washing well 606 to a level that is at least the level that a reagent or sample is drawn into probe 400 during use, e.g., the level 902. Drawing the cleaning liquid into probe 400 from washing well 106 simulates drawing a reagent or sample into probe 400 during use. For one embodiment, the cleaning liquid is drawn into probe at about the same rate as a sample or reagent is drawn in during use.

The internal probe wash described above is then performed. That is, additional cleaning liquid is forced through probe 400 into washing well 606 to expel any cleaning liquid previously contained in the probe into washing well 606. As the cleaning liquid is forced through probe 400, probe 400 is extracted from washing well 606 at a relatively low extraction rate, and valve 684 is opened so that a vacuum is applied to drying section 660 via aspiration channels 664, radial channel 585, and manifold 668 (FIG. 10). The vacuum causes air to flow over the exterior surface 430 of probe 400. This airflow acts to dry exterior surface 430 as probe 400 is extracted. For one embodiment, the extraction rate is less than the insertion rate, e.g., about ¼ the insertion rate. The relatively low extraction rate increases the residence time of the probe within drying section 660, which results in more complete drying of the probe exterior. Note that for one embodiment, internal probe washing, drying the probe exterior, and extracting the probe from washing well 606 occur substantially simultaneously. For another embodiment, probe 400 is extracted after the cleaning liquid is forced through probe 400.

For other embodiments, valve 696 (FIG. 8) is opened at the start of the internal probe wash, while a vacuum is applied to manifold 668, for a preselected time sufficient to substantially empty washing well 606 by aspirating the cleaning liquid from the washing well 606 through radial channel 694, valve 696, and manifold 688 (FIG. 8). For some embodiments, washing well 606 is emptied substantially faster than the cleaning liquid is added to washing well 606. After valve 696 is closed, the cleaning liquid flows through probe 400, as probe 400 is extracted, and fills washing well 606 to the level 902, e.g., to substantially to inlet plane 662 (FIG. 11) of washing well 606. For one embodiment, washing well 606 is filled and drained multiple times during the internal probe wash.

For one embodiment, the volume of cleaning liquid that passes through probe 400 during the internal probe wash exceeds the volume of washing well 606 and the excess cleaning liquid is drawn through drying section 660 and manifold 688 (FIG. 10) and/or through radial channel 694, valve 696, and manifold 688 (FIG. 8) while extracting probe 400 from washing well 606.

For some embodiments, if end 405 of probe 400 is extracted to about inlet plane 662 of washing well 606 before the end of the internal probe wash, i.e., before the cleaning liquid stops flowing through probe 400, extraction of probe 400 is stopped with end 405 substantially at inlet plane 662 (FIG. 11) until the cleaning liquid stops flowing. Any excess cleaning liquid that flows through probe 400 into the washing well is drawn through drying section 660 and manifold 688 and/or through radial channel 694, valve 696, and manifold 688 while probe 400 is stopped at this position. Extraction of probe 400 then continues until end 405 is relocated between inlet plane 670 of central channel 666 and end 602, as shown in FIG. 11.

For another embodiment, prior to the internal probe wash described above (i.e., prior to forcing additional cleaning liquid through probe 400) some of the cleaning liquid is expelled, e.g., about ½ to all of the cleaning liquid, into washing well 106 or 606 from the probe with the probe at a fixed position. This can occur multiple times by drawing cleaning liquid from washing well into the probe and then expelling the cleaning liquid into the washing well prior to forcing additional cleaning liquid through probe 400. For some embodiments, the acceleration of the cleaning liquid while it is expelled is about 3 to 5 times greater than the acceleration while forcing additional cleaning liquid through probe 400 during the internal probe wash. The deceleration of the cleaning liquid to stop the expulsion may also be about 3 to 5 times greater than the deceleration of cleaning liquid during the internal probe wash.

For some embodiments, prior to forcing additional cleaning liquid through probe 400 during the internal probe wash, the probe is oscillated in an up and down motion within washing well 106 or 606. Note that during the oscillations, the probe contains the cleaning liquid. For another embodiment, the cleaning liquid contained within washing well 106 or 606 and/or the cleaning liquid contained in the probe is excited, prior to forcing additional cleaning liquid through probe 400 during the internal probe wash, while the probe is inserted in the washing well. This may be accomplished using a sonic or ultrasonic device and/or by pulsating the vacuum applied to drain 108 or manifold 688.

The above-described probe cleaning methods are not limited to wash cups 100 and 600, e.g., wash cups having integral washing wells and waste cups. Rather, the probe cleaning methods can be used with separate wash cups, one functioning as a waste cup, the other functioning as a washing well.

For another embodiment, waste cup 112 or 612 may be eliminated. For this embodiment, the operations associated with the waste cup are performed with washing well 106 or 606. That is, the probe is positioned above the washing well, as shown in FIG. 4 or 11, and is filled with the cleaning liquid without allowing the cleaning liquid to flow through probe 400 into the washing well. Alternatively, the flow is allowed to flow through probe 400 into the washing well for expelling a contaminant from the probe interior into the washing well and then stopped, with the cleaning liquid filling the probe interior. The washing well is then flushed with cleaning liquid and is filled prior to inserting the probe therein.

Figure 12:
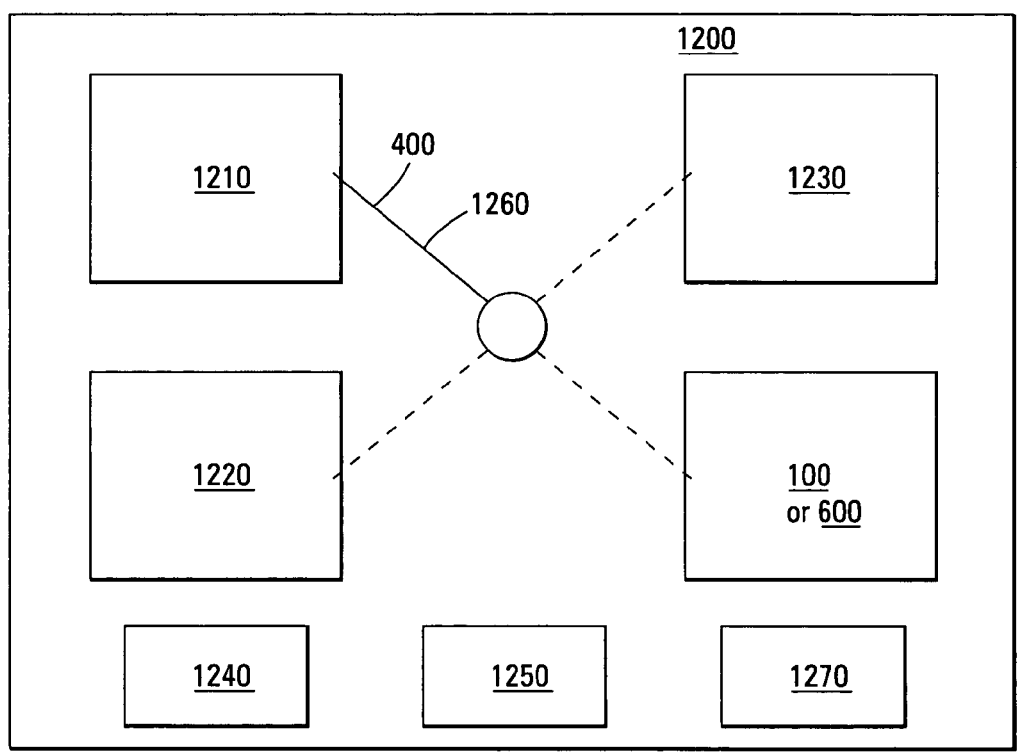
FIG. 12 is a block diagram of a medical analyzer, according to another embodiment of the present invention.

FIG. 12 is a block diagram illustrating an automated medical analyzer 1200, such as an immunoassay analyzer, according to another embodiment of the present invention. Analyzer 1200 includes a sample region 1210 for receiving sample vials containing liquid samples, such as blood, urine, etc. Sample region 1210 may include a carousel for receiving and moving the sample vials. Analyzer 1200 may include a reagent region for receiving vials of various reagents. Reagent region 1220 may include a carousel for receiving and moving the reagent vials. Analyzer 1200 includes a tester (or reactor) 1230 that may include test tubes carried on a carousel. Analyzer 1200 includes wash cup 100 or 600, as described above. For various embodiments, analyzer 1200 includes a vacuum system 1240, e.g., pumps and/or syringes, and a pumping station 1250, e.g., pumps and syringes, for supplying positive gage pressures. For another embodiment, analyzer 1200 has a robot arm 1260 for positioning a hollow probe, such as the probe 400 described above, in the sample area 1210, reagent area 1220, reactor 1230, and wash cup 100 or 600. Analyzer 1200 also includes a controller 1270 for controlling operation of the analyzer. For one embodiment, the controller is adapted to activate the valves 114 and 116 of FIG. 1 or the valves 684, 692, and 696 of FIG. 8. For one embodiment, pumping station 1250 is fluidly connected to a cleaning-liquid reservoir (not shown) of analyzer 1200 for pumping cleaning liquid from the cleaning-liquid reservoir to the hollow probe and to the washing wells of the wash cups.

In operation, for one embodiment, robot arm 1260 positions probe 400 in a sample vial contained in sample region 1210, and a sample is drawn into probe 400. Robot arm 1260 then moves probe 400 to reactor 1230, and the sample is dispensed into a test tube, for example. Robot arm 1260 then moves probe 400 to wash cup 100 or 600 for cleaning, as described above. After probe 400 is cleaned, robot arm 1260 may position probe 400 in a reagent vial contained in reagent region 1220, and a reagent is drawn into probe 400. Robot arm 1260 then moves probe 400 to reactor 1230, and the reagent is dispensed into the test tube containing the sample and a reaction occurs. Robot arm 1260 then moves probe 400 to wash cup 100 or 600 for cleaning, thus readying probe 400 for another operation.

CONCLUSION

Although specific embodiments have been illustrated and described herein, it will be appreciated by those of ordinary skill in the art that any arrangement that is calculated to achieve the same purpose may be substituted for the specific embodiments shown. Many adaptations of the invention will be apparent to those of ordinary skill in the art. Accordingly, this application is intended to cover any adaptations or variations of the invention. It is manifestly intended that this invention be limited only by the following claims and equivalents thereof.

What is claimed is:

1. A method of cleaning a hollow probe having a tip, comprising:
   aligning the probe with a waste cup of a probe washing cup, said probe washing cup having a waste cup and a washing well;
   then flowing cleaner through the probe into the waste cup to expel a substance within the probe into the waste cup;
   then stopping the flow of cleaner through the probe, wherein the probe is filled with the cleaner when the flow is stopped;

then drawing air into the hollow probe through the tip of the hollow probe while moving the probe, partially filled with cleaner, from the waste cure to a position above a drying section:

then inserting a length of the probe partially filled with cleaner, into the washing well containing an additional cleaner;

then drawing the additional cleaner from the washing well into the probe;

then flowing the additional cleaner through the probe into the washing well; and extracting the probe from the washing well; and directing a forced airflow over an exterior of the probe in the drying section while extracting the probe from the washing well, where the forced airflow acts to dry the exterior of the probe.

2. The method of claim 1, wherein aligning the probe with the waste cup further comprises positioning a tip of the probe at a level above the waste cup that is between an inlet plane of the drying section and the open end of the probe washing cup.

3. The method of claim 2, wherein moving the probe from the waste cup to the position above the drying section of the probe washing cup, comprises keeping the tip of the probe at a fixed distance from the open end of the probe washing cup while moving the probe from the waste cup to the position above a drying section.

4. The method of claim 1, further comprising draining the cleaner from the washing well while flowing the additional cleaner through the probe into the washing well.

5. The method of claim 1, further comprising filling the washing well using the additional cleaner while extracting the probe from the washing well.

6. The method of claim 1, wherein directing a forced airflow over an exterior of the probe in the drying section is accomplished by applying a vacuum to the drying section.

7. The method of claim 1, further comprising drawing cleaner from the washing well into the drying section and out of the wash cup while extracting the probe from the washing well.

8. The method of claim 1, wherein drawing the cleaner from the washing well into the probe further comprises drawing the cleaner from the washing well into the probe at a rate that is about the same rate as the substance is drawn into the probe when the probe is in use.

9. The method of claim 1, wherein forcing additional cleaner through the probe into the washing well expels the cleaner drawn from the washing well into the probe.

10. The method of claim 1, further comprising expelling at least a portion of the cleaner drawn from the washing well into the probe from the probe into the washing well before forcing additional cleaner through the probe into the washing well.

11. The method of claim 1, further comprising continuing to force the additional cleaner through the probe into the washing well while extracting the probe.

* * * * *